(12) United States Patent
Cutler et al.

(10) Patent No.: US 8,932,876 B2
(45) Date of Patent: Jan. 13, 2015

(54) METHOD AND SYSTEM FOR PURIFYING CHARGED RADIOISOTOPES

(75) Inventors: Cathy Sue Cutler, Columbia, MO (US); Gary John Ehrhardt, Columbia, MO (US); Hendrik Petrus Engelbrecht, Columbia, MO (US); Delbert E. Day, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 1244 days.

(21) Appl. No.: 12/454,003

(22) Filed: May 11, 2009

(65) Prior Publication Data

US 2014/0369903 A1 Dec. 18, 2014

Related U.S. Application Data

(60) Provisional application No. 61/127,094, filed on May 9, 2008.

(51) Int. Cl.
| | |
|---|---|
| *B01D 15/36* | (2006.01) |
| *G21H 5/02* | (2006.01) |
| *G21G 1/00* | (2006.01) |
| *A61K 51/00* | (2006.01) |
| *G21G 4/08* | (2006.01) |

(52) U.S. Cl.
CPC ............ *G21G 1/0005* (2013.01); *B01D 15/363* (2013.01); *G21H 5/02* (2013.01); *A61K 51/00* (2013.01); *G21G 4/08* (2013.01); *B01D 15/362* (2013.01)
USPC .......................................................... 436/174

(58) Field of Classification Search
CPC .............. G01N 2001/2826; G01N 2001/4011; G01N 30/96; B01D 15/362; B01D 59/30; B01D 15/363; C22B 26/20; C22B 59/00; G21F 9/007; G21F 9/12; G21G 1/001; G21G 1/0005; G21G 4/08; A61K 51/00; G21H 5/02
See application file for complete search history.

(56) References Cited

U.S. PATENT DOCUMENTS 5,154,897 A * 10/1992 Ehrhardt et al. ................... 423/6
2008/0035542 A1 * 2/2008 Mourtada et al. ............. 210/143

OTHER PUBLICATIONS

HEPES Wikipedia entry, obtained by the examiner at <http://en.wikipedia.org/wiki/HEPES> on Feb. 7, 2013.*
Loc'h, C. et al. "A new generator for ionic gallium-68." J. Nucl. Med. (1980) 21 171-173.*
Nakayama, M. et al. "A new 68Ge / 68Ga generator system using an organic polymer containing N-methylglucamine groups as adsorbent for 68Ge." Applied Radiation and Isotopes (2003) 58 9-14.*
Supelco Product Bulletin 882A. "Mobile Phases for Ion Exchange Chromatography and Chromatofocusing." Sigma-Aldrich Co., 1995.*
Solvent Wikipedia Article, obtained by the examiner from <http://wikipedia.org> on Jan. 30, 2014.*

* cited by examiner

*Primary Examiner* — Christopher A Hixson
(74) *Attorney, Agent, or Firm* — Stinson Leonard Street LLP

(57) ABSTRACT

The present invention provides a simple and inexpensive method for removing metal and other impurities in a radioisotope solution. The invention further includes the development of a new parent/daughter generator system for collecting the daughter isotope in a concentrated solution.

19 Claims, 3 Drawing Sheets

METHOD AND SYSTEM FOR PURIFYING CHARGED RADIOISOTOPES

CROSS-REFERENCE TO RELATED APPLICATIONS

This application claims the benefit of U.S. Provisional Application Ser. No. 61/127,094, entitled "Method and System for Purifying Charged Radioisotopes," to Cutler, et al., filed on May 9, 2008.

GRANT STATEMENT

This invention was made in part from government support under Grant No. SP50CA103130-04 from the National Institutes of Health. The U.S. Government has certain rights in the invention.

FIELD OF INVENTION

The present invention relates to method and system for purification and collection radioisotopes. More specifically, the present invention relates to extracting and collecting a daughter isotope from a +2 parent strong base/+3 daughter weak base source and purification of charged radioisotopes.

BACKGROUND OF INVENTION

There is a renewed interest in high specific activity radionuclides in concentrated form, free of cold metal contaminants. One example is the Ge-68/Ga-68 generator systems for diagnostic nuclear medicine due to the spread of PET (Positron Emission Tomography) scanners for $^{18}$F FDG studies, which require a cyclotron-independent source of short-lived, positron-emitting isotope for the expanding area of receptor-specific imaging and therapy. The benefits offered by the Ge-68/Ga-68 generator system, such as the long half-life of Ge-68 (270.8 days), short half-life of Ga-68 (68 min) along with Ga-68's high positron yield, and lack of high energy gamma rays, make the system very convenient for PET. Furthermore, Ga-68 chemistry is dominated by the +3 oxidation state and is readily chelated by ligands, such as NOTA (1, 4, 7-triaazacyclononane-1,4,7-triacetic acid) and DOTA (1,4,7,10-tetraazacyclododecane-1,4,7,10-tetraacetic acid), which are also used to chelate radiolanthanides for use as radiopharmaceuticals.

The current commercial generators utilize Ge-68 (germanate) adsorbed onto either tin dioxide or titanium dioxide; Ga-68 is then eluted with 0.1 to 1N HCl. Unfortunately, the generators require high volumes of acid to elute the Ga-68, generally in the 5 to 20 ml range, and the eluates contain trace levels of metals such as iron, zinc, and/or titanium. The metal impurities, though present in very low levels, are also chelated by ligands, such as DOTA, and thus compete with Ga-68 for the limited number of binding sites on the target cells resulting in decreased contrast and quality of the images. Additionally it can result in higher uptake to normal tissues and, for peptides that are potent agonists, result in toxic side effects. Furthermore, it can lead to increased cost due to the excess of biomolecule that is needed which is often the most costly component of the drug.

Therefore, there is a need to provide a new and improved method and system to extract, purify, and collect a daughter isotope, from a parent/daughter source, in a relatively concentrated form and with minimum metal or other impurities.

There is also a need to provide a new and improved method/system to purify and collect a high specific activity radioisotope in general.

SUMMARY OF INVENTION

The invention provides a novel and improved method to purify and collect a radioisotope in a relatively concentrated form with significantly decreased metal or other contaminations. The inventive method for purifying a desired radioisotope from a contaminated radioisotope solution includes the steps of 1) providing an acid-treated glass-beads/spheres column, whereas the glass-beads/spheres are specially engineered to contain low ppm-ppb quantities of metal impurities and treated with a first pre-selected acid for a predetermined time period before packing, 2) preparing a loading solution by adjusting the pH of the contaminated radioisotope solution to above about 4, preferably between about 5 to 6, and adding a pre-selected modifier, whereas the modifier is selected for its ability to dissolve contaminants, 3) administering the loading solution onto the column, 4) performing a wash by passing a pre-selected wash solution, and 5) eluting the desired radioisotope off the column with a second pre-selected acid.

In a specific aspect, the invention provides a new and improved method to extract and purify a daughter radioisotope from a parent/daughter radioisotope stock solution. The inventive method includes the steps of 1) providing an acid-treated glass-beads/spheres column, 2) preparing a parent/daughter loading solution by adjusting the pH of a parent daughter stock solution to above about 4 and adding a pre-selected modifier, whereas the modifier is selected for its ability to dissolve more parent isotope over daughter isotope, 3) administering the parent/daughter loading solution onto the column, 4) performing a wash by passing a pre-selected wash solution, and 5) eluting the daughter isotope off the column with a pre-selected acid.

In one embodiment, a daughter isotope, Ga-68, may be collected from a Ge-68/Ga-68 parent/daughter stock solution. Particularly, the glass beads/spheres may be pre-treated with acid, such as 6 M HCl, for 5 days in a soxhelt apparatus to remove any remaining stray metal contaminants. The glass beads/spheres employed may be borosilicate glass spheres or $SiO_2$ beads that have been specially engineered to contain low ppm-ppb quanitities of metal impurities with a diameter between about 20 to 75 µm. The column may be packed with about 0.1 to about 5 mL of the desired glass spheres. The stock solutions may be brought to a pH above about 4, preferably between 5 to 6, with any suitable base, such as ultra pure NaOH or $NH_4OH$. The modifier employed may be ultra-pure organics such as acetone, ethanol, DMSO or others miscible with water that could change the dielectric properties of the medium and increase the activity coefficient of the radionuclide of interest relative to that of the impurity driving the radionuclide onto the column or buffers, such as HEPES, ammonium acetate or sodium acetate. Additionally etching of the glass beads using HF or sulfuric acid may aid in opening up hydroxyl groups to aid in the selective extraction process. The wash solution may be pH adjusted ultra-pure water with or without ultra-pure organics or buffers. The eluant may be about 0.1 N HCl solution in a small amount, such as about 0.1 mL.

The invention further provides a novel and improved parent/daughter isotope (such as Ge-68/Ga-68) generator system, which is comprised of a generator column containing a parent/daughter stock solution at a pH above 4 on pre-treated glass spheres, a first sealed eluant container of water or other solution with pH above about 4, and a second sealed eluant container of an acid solution.

DETAILED DESCRIPTION OF INVENTION

Figure 1:
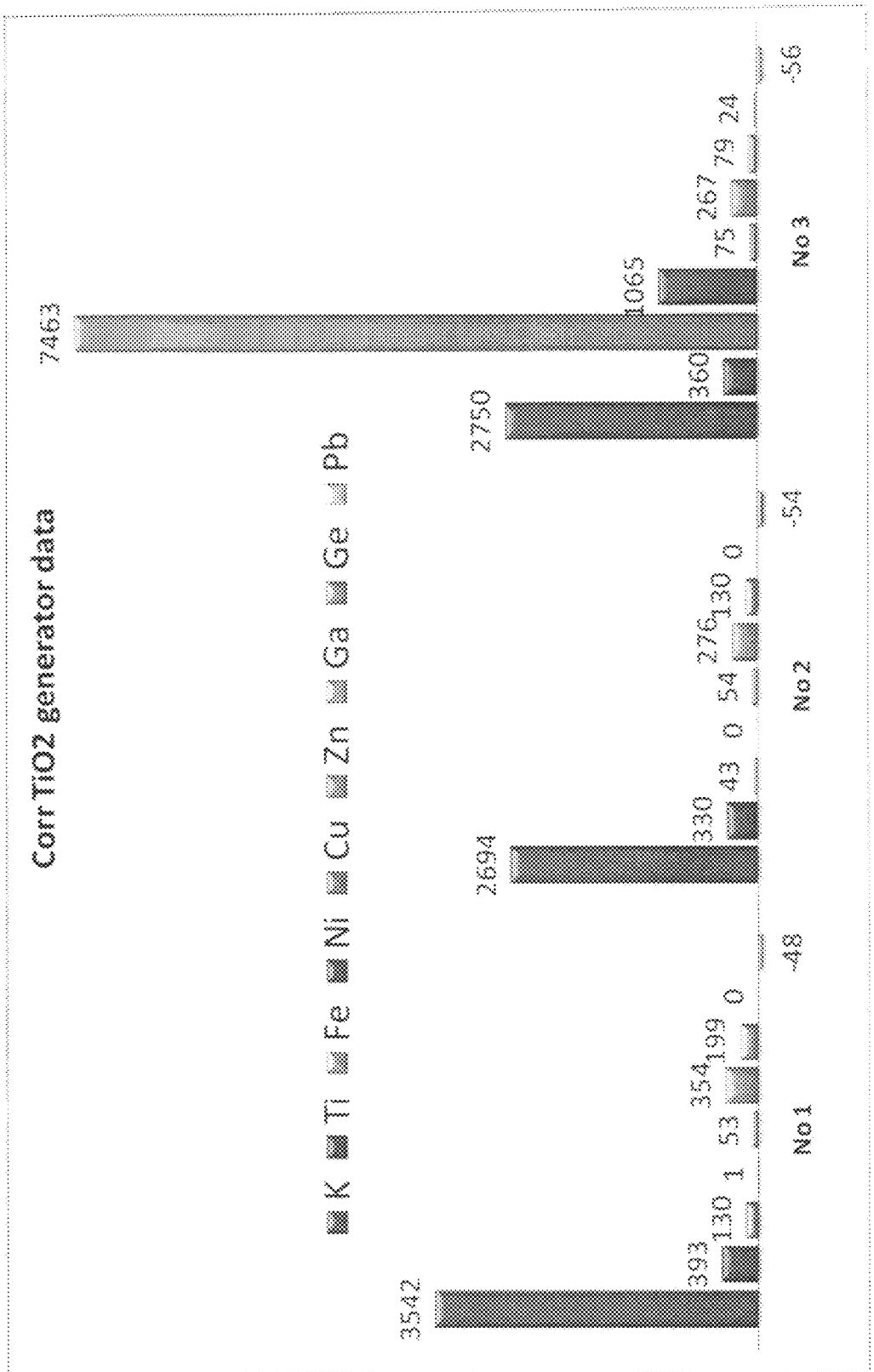
FIG. 1 shows the ICP-OES results obtained of metals present in the eluants of the first generation commercial Oblinsk Ge-68/Ga-68 generator.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

The invention provides a novel method for purifying and collecting a radioisotope for imaging and therapeutic use in a relatively concentrated form. Particularly, the inventive method includes the steps of 1) providing an acid-treated glass-beads/spheres column, whereas the glass-beads/spheres are specially engineered to contain low ppm-ppb quantities of metal impurities and treated with a first pre-selected acid for a predetermined time period before packing, 2) preparing a loading solution by adjusting the pH of the contaminated radioisotope solution to above about 4, preferably between about 5 to 6, and adding a pre-selected modifier, whereas the modifier is selected for its ability to dissolve contaminants and aid in adsorption of the radionuclide of interest onto the beads, 3) administering the loading solution onto the column, 4) performing a wash by passing a pre-selected wash solution, and 5) eluting the desired radioisotope off the column with a second pre-selected acid.

The inventive purification method may be applied to purify Ga-67, Ga-68, Sr-90/Y-90, Ca-47/Sc-47, Ra-224/Pb-224. Cu/Zn and any +2 parent strong base/+3 daughter weak base system as well as radiolanthanides and other charged radioisotopes. For example, a feasibility study has been performed with a contaminated Ga-67 on a small 0.2 mL borosilicate column. Specifically, the borosilicate glass beads were cleaned by refluxing in 6 M HCl for 5 days in a soxhlet apparatus. The glass-beads/spheres were loaded into an acid washed column. The column was pre-equilibrated/washed with water until the eluant was above pH 5. The contaminated Ga-67 sample was neutralized to pH~9 by the addition of Optima (ultra pure) ammonium hydroxide. The Ga-67 sample was loaded onto the glass-beads/spheres column and allowed to pass through. The column was washed with Milli-Q water (5 mL) to remove any metal contaminants that co-absorbed/co-precipitated with the Ga-67 onto the glass-beads/spheres. The purified Ga-67 was eluted with Optima (ultra pure) 0.3 mL 0.1 M HCl.

Table 1 lists metal impurities detected by ICP-OES in Ga-67 before and after the feasibility study.

TABLE 1

Metal impurities detected by ICP-OES in Ga-67 before and after purification

| | Unpurified Ga-67 | Purified Ga-67 (300 µL strip sol) |
|---|---|---|
| Zn | 10 562 | 7 048 |
| Ga | 77 | 69 |
| Ge | 125 | 60 |
| Pb | 710 | 4 010 |
| Ca | 569 | 306 |
| Fe | 171 | 70 |
| Ni | 1 | 17 |
| Cu | 747 | 572 |
| Na | 2678 | 126 |

As shown in Table 1, all the metal impurities except Ni and Pb have been lowered after the purification. The increases in Ni and Pb are due to the use of borosilicate beads that contained both Ni and Pb. The data indicates that when a larger column with specially engineered beads (that contain low ppb levels of metals) can remove most of the remaining metal impurities without introducing any new impurities. Modifiers were not used in the feasibility study, but may be added to improve the purification.

The invention also provides a method for purifying a daughter isotope from a parent/daughter stock solution, such as Ge-68/Ga-68. The inventive method includes the steps of 1) providing an acid-treated glass-beads/spheres column, 2) preparing a parent/daughter loading solution by adjusting the pH of a parent daughter stock solution to above about 4 and adding a pre-selected modifier, whereas the modifier is selected for its ability to dissolve more parent isotope over daughter isotope, 3) administering the parent/daughter loading solution onto the column, 4) performing a wash by passing a pre-selected wash solution, and 5) eluting the daughter isotope off the column with a pre-selected acid.

The invention teaches that a daughter product (such as Ga-68) is radiocolloidal, and that its +3 ion (such as Ga-68+3) becomes highly absorptive to hydroxyl groups on surfaces such as glass or other related surfaces at pH values above about 4. On the other hand, the parent isotope (such as Ge-68) is readily soluble at pH above 4. Thus, a column filled with borosilicate glass microspheres, or silicon dioxide will extract a significant portion of the daughter isotope (such as Ga-68) from an equilibrated solution while passing the parent isotope (such as Ge-68) and other metals unabsorbed.

The invention further provides a novel and improved parent/daughter generator system to produce concentrated daughter isotope with low metal contamination. The inventive generator, also called as the Fajan's adsorption generator, comprised of a generator column containing a parent/daughter mixed solution at a pH above 4 on pre-treated glass spheres, a first sealed eluant container of water or other solution with pH above about 4, and a second sealed eluant container of an acid solution.

The inventive purification method and the Fajan's adsorption generator provide the advantage of only requiring purified water and ultra-pure acid as eluant, thus limits the introduction of stray metal ions into the desired isotope product. The inventive method and the Fajan's adsorption generator further provide the advantage of collecting a desired isotope in a relatively high concentration, which may be used directly in radiopharmaceuticals.

The invention further provides an example of using the inventive generator and method for generating, purifying, and collecting Ga-68 from a Ge-68/Ga-68 solution. Particularly, borosilicate glass spheres (20-75 μm) and $SiO_2$ were cleaned by refluxing in 6 M HCl for 5 days in a soxhlet apparatus to remove any stray metal contamination. Columns were packed with 0.1-5 mL of borosilicate glass or $SiO_2$. Germanium-68 or Ga-68 solutions in 0.1 mL-10 mL were brought to pH 5-6 with either ultrapure NaOH or $NH_4OH$. Modifier(s), such as acetone, DMSO, acetonitrile, ethanol, N-methylglucamine, or other organics or buffer, may be added depending on the type(s) of contamination. Solutions were then loaded onto the column and allowed to pass through the glass beads, recovering it for reuse of Ge-68. The column is then rinsed with 5-10 ml of ultrapure water (18 $M\Omega cm^{-1}$ resistivity) at a pH of 5-6. The rinse step removes any remaining Ge-68 and other trace metals. The Ga-68 is then stripped off the column with 0.1 N HCl (0.1-1 mL).

Figure 2:
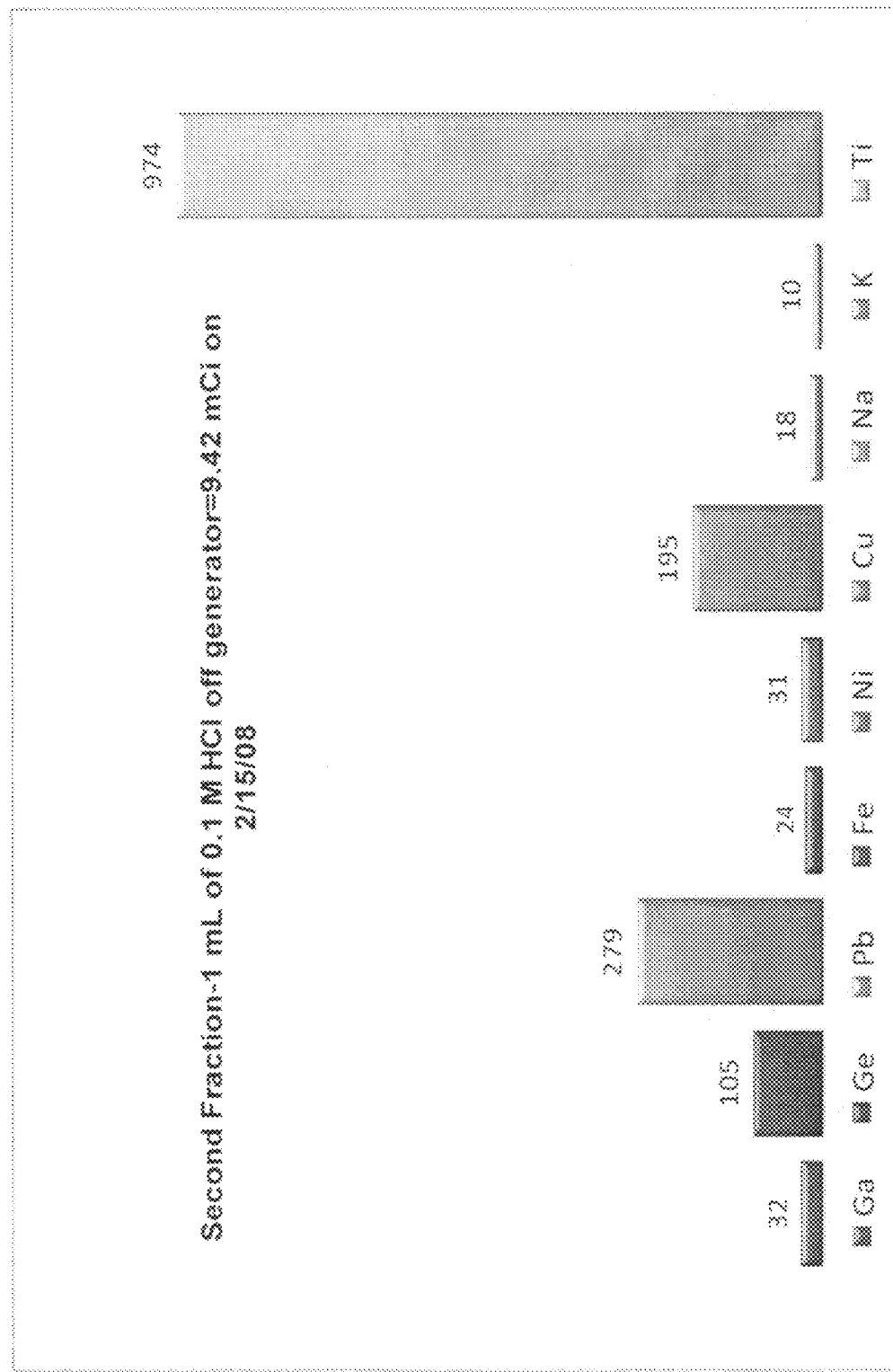
FIG. 2 shows the ICP-OES results obtained of metals present in the eluants of the second generation commercial Oblinsk Ge-68/Ga-68 generator.

The metal impurities in the eluate obtained from the inventive generator have been analyzed using ICP-OES and ICP-MS and compared with the results obtained by two generations of the commercial Oblinsk Ge/Ga generators. FIG. 1 shows the ICP-OES results obtained of metals present in the eluate of the first generation commercial Oblinsk Ge/Ga generator. As can be seen in FIG. 1, the metal impurity levels are significant and increase with time. FIG. 2 shows the ICP-OES results obtained of metals present in the eluate of the second generation commercial Oblinsk Ge/Ga generator, where the metal components (septum and needles) were replaced. The levels of metal impurities have been decreased somewhat by changing to luer lock connections.

Figure 3:
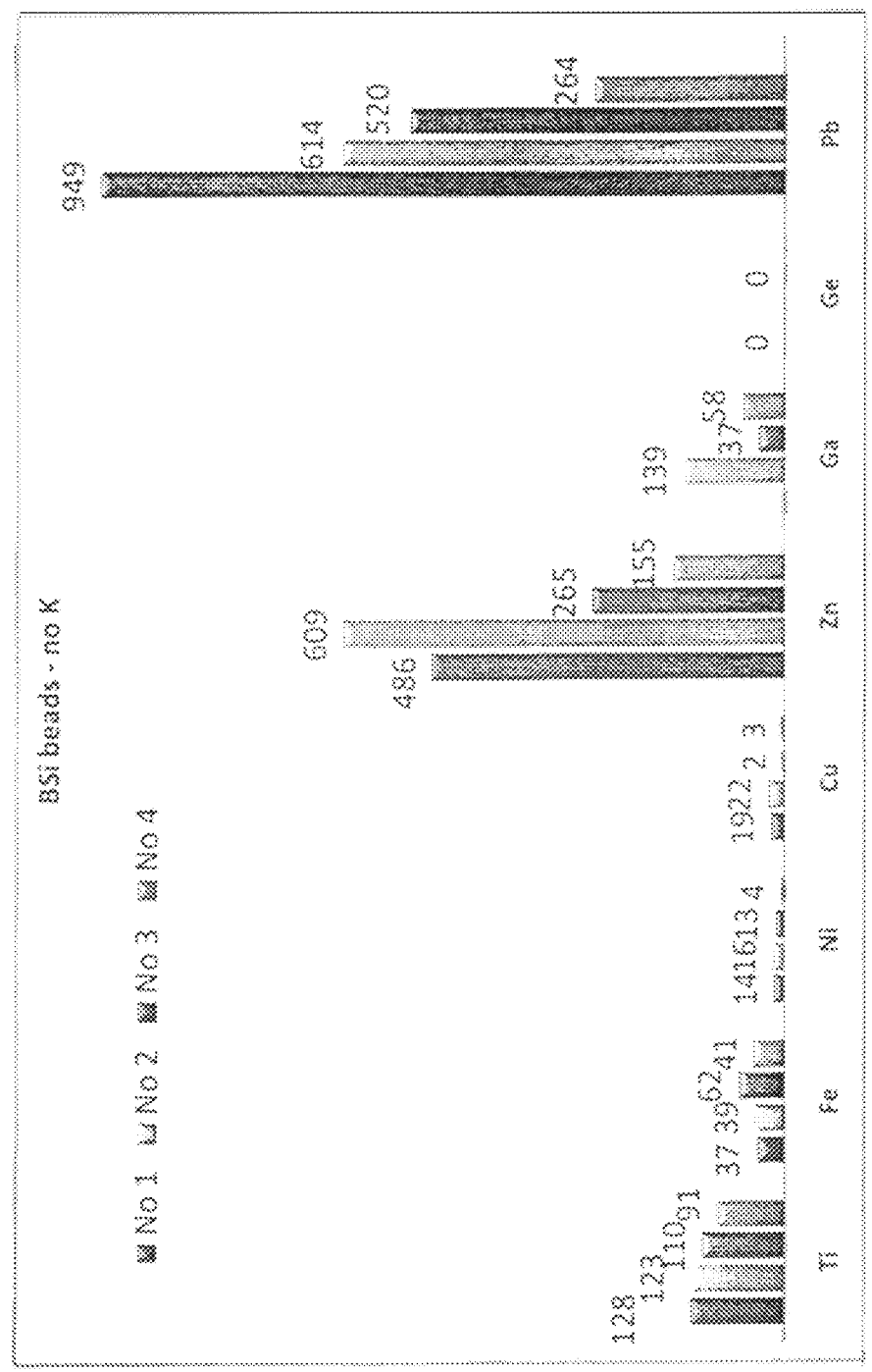
FIG. 3 shows the ICP-OES results obtained of metals present in the eluants of the inventive Fajan's adsorption generator.

FIG. 3 shows the ICP-OES results obtained of metals present in the eluate of the inventive generator. The metal impurities, except for Pb and Zn, are lower and all decrease with subsequent elutions. The Pb and Zn values varied based on the absorbant material. Since metal impurities steadily decrease in subsequent elutions of the adsorption generators it may actually improve with time, unlike the commercial generator, which results in lower radiolabeling yields with time.

The detail of the invention is also described in the attached article, titled "Development and Evaluation of a Novel $^{68}$Ga Generator," which is hereby incorporated in its entirety.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

The invention claimed is:

1. A method for generating an eluate containing daughter isotope in ionic form from a parent/daughter isotope solution, said method comprising:
   a) providing an acid-treated glass adsorbent column,
   b) providing a loading solution by adjusting the isotope solution to a pH of above about 4.0,
   (c) adding N-methylglucamine to the loading solution to change the dielectric properties of the loading solution and increase the activity coefficient of the daughter isotope relative to the to the parent isotope to increase selective adsorption of the daughter isotope onto the column over the parent isotope,
   d) loading the column with the loading solution,
   e) rinsing the loaded column with water to elute off the parent isotope, and
   f) eluting the daughter isotope in a solution by rinsing the column with an acid solution.

2. The method of claim 1, wherein said glass comprises spheres-rich in OH groups.

3. The method of claim 1, wherein said acid solution of said eluting step comprises 0.1N HCl.

4. The method of claim 1 wherein said step of providing said acid-treated glass adsorbent column comprises treating said glass with hydrochloric acid, hydrofluoric acid, or sulfuric acid.

5. The method of claim 1 wherein said glass adsorbent comprises glass spheres or $SiO_2$ beads having a diameter between about 20 to 75 micron.

6. The method of claim 1 wherein said loading solution has a pH of about 5 to 6.

7. The method of claim 1 wherein said loading solution has a pH of about 9.

8. The method of claim 1 wherein said loading solution comprises sodium hydroxide or ammonium hydroxide.

9. The method of claim 1 wherein said isotope solution comprises a +2 parent strong base and +3 daughter weak base system.

10. The method of claim 1 where said isotope solution comprises Ge-68 and Ga-68 and wherein said daughter isotope is Ga-68.

11. The method of claim 1 wherein said isotope solution comprises Y-90 and Sr-90 and said daughter isotope is Y-90.

12. The method of claim 1 wherein said isotope solution comprises Ca-47 and Sc-47 and said daughter isotope is Sc-47.

13. The method of claim 1 wherein said eluting step is performed with hydrochloric acid.

14. The method of claim 1 wherein an additional modifier is added to the loading solution, selected from the group consisting of acetone, DMSO, acetonitrile, ethanol, N-methylglucamine, and HEPES, ammonium acetate, and sodium acetate.

15. The method of claim 14 wherein said additional modifier comprises acetone.

16. The method of claim 14 wherein said additional modifier comprises DMSO.

17. The method of claim 14 wherein said additional modifier comprises acetonitrile.

18. The method of claim 14 wherein said additional modifier comprises ethanol.

19. The method of claim 14 wherein said additional modifier comprises HEPES.

* * * * *